United States Patent
Kristbjarnarson et al.

(10) Patent No.: US 6,461,307 B1
(45) Date of Patent: Oct. 8, 2002

(54) DISPOSABLE SENSOR FOR MEASURING RESPIRATION

(75) Inventors: Helgi Kristbjarnarson; Kormakur Hermannson; Eggert Gudjonsson, all of Reykjavik (IS)

(73) Assignee: Flaga hf, Reykjavik (IS)

( * ) Notice: Subject to any disclaimer, the term of this patent is extended or adjusted under 35 U.S.C. 154(b) by 0 days.

(21) Appl. No.: 09/661,156

(22) Filed: Sep. 13, 2000

(51) Int. Cl.[7] .................... A61B 5/08; A61B 5/103; A61B 5/117
(52) U.S. Cl. .................... 600/534; 600/529; 600/595
(58) Field of Search .................... 600/534, 535, 600/529, 300, 587, 390, 547, 595

(56) References Cited

U.S. PATENT DOCUMENTS

| | | | |
|---|---|---|---|
| 3,279,465 A | | 10/1966 | Cherio et al. |
| 3,307,546 A | | 3/1967 | Cherio et al. |
| 3,560,845 A | | 2/1971 | Goldberg et al. |
| 4,308,872 A | | 1/1982 | Watson et al. |
| 4,373,534 A | | 2/1983 | Watson |
| 4,452,252 A | * | 6/1984 | Sackner ........... 600/534 |
| 4,807,640 A | | 2/1989 | Watson et al. |
| 4,815,473 A | * | 3/1989 | Watson et al. ........... 600/534 |
| 4,817,625 A | | 4/1989 | Miles |
| 5,159,935 A | * | 11/1992 | Sackner et al. ........... 600/534 |
| 5,241,300 A | * | 8/1993 | Buschmann ........... 340/573.1 |
| 5,301,678 A | * | 4/1994 | Watson et al. ........... 600/534 |
| 5,331,968 A | * | 7/1994 | Williams et al. ........... 600/534 |
| 5,611,349 A | | 3/1997 | Halleck et al. |
| 5,701,370 A | * | 12/1997 | Muhs et al. ........... 385/13 |
| 5,913,830 A | * | 6/1999 | Miles ........... 600/535 |

* cited by examiner

Primary Examiner—Kevin Shaver
Assistant Examiner—Navin Natnithithadha
(74) Attorney, Agent, or Firm—Pillsbury Winthrop LLP

(57) ABSTRACT

The present invention is directed to a disposable sensor for monitoring and measuring the respiration of a patient. The disposable sensor includes at least one flexible ribbon adapted to encircle a portion (e.g., the chest or abdomen) of the patient. Each flexible ribbon includes a conductor strip secured thereto. The conductor strip extends in a zig-zag or other predetermined pattern. The disposable sensor also includes a connector assembly for connecting and securing a first free end of the ribbon to a second free end of the ribbon. The connector assembly is operatively coupled to the conductor, and is further adapted to be connected to a monitoring device.

20 Claims, 7 Drawing Sheets

DISPOSABLE SENSOR FOR MEASURING RESPIRATION

FIELD OF THE INVENTION

The present invention relates to a disposable sensor for use in measuring respiration of a patient. In particular, the present invention relates to a respiratory inductive plethysmograph ("RIP") disposable sensor formed from a flexible stretchable ribbon having a conductor secured thereto. The disposable sensor is cut to size by a health care provider sized to encircle a patient to measure respiration. The present invention also relates to a connector assembly for the disposable sensor that releasably grips the conductor of the sensor.

BACKGROUND OF THE INVENTION

Respiratory inductive plethysmograph monitoring apparatus are used to measure and monitor the respiration of a patient. Typically, the RIP monitoring apparatus includes a conductive loop closely encircling a body member. The inductance of the conductive loop is a measure of the cross sectional area encircled. Changes in inductance reflect the respiration of the patient. The conductive loop is connected to an electronic monitoring device, which includes circuitry that reliably and accurately measures changes in the inductance of the conductive loop mounted on the body. Respiratory movements of the wearer result in changes in the cross-sectional areas and hence in the inductance of the conductive loop. Once these changes in inductance are converted to an electrical signal for the conductive loop, the signal is calibrated by the electronic monitoring device to accurately measure the volume of respiration. To ensure accurate monitoring of the patient's respiration, it is important that the conductor loop fit snugly about the patient's torso such that the expansions and contractions of the conductor closely follow the expansions and contractions of the chest and abdomen. Further, since it is impractical to render the conductors expandable, some other mechanism for accommodating expansion and contraction of the conductors must be employed.

U.S. Pat. No. 4,308,872 to Watson et al entitled "Method and Apparatus for Monitoring Respiration" discloses an apparatus for monitoring respiration. In one embodiment, the monitoring apparatus includes a tubular stretch bandage in the form of a long sleeveless sweater worn closely fitted over the torso of a patient. A conductor is attached to the sweater in a number of turns around the torso from the lower abdomen to the upper chest, and so will provide a measure of area averaged over the entire torso. More turns may be placed over one portion of the torso and fewer over other portions, if it is desired to give greater weight to changes in area of one portion of the torso relative to others. The multi-turn loop is closed by a vertical section returning to the starting point. Both ends of the loop are electrically connected to an electronic circuit module, which is located on the patient's lower side. In another embodiment, the monitoring apparatus includes two elastic tubes located about the upper chest and the lower abdomen of the patient. Conductors are mounted in a single turn loop circumferentially of tubes. Snap fasteners are provided for holding the band together.

U.S. Pat. No. 4,807,640 to Watson et al., entitled "Stretchable Band-Type Transducer Particularly Suited For Respiration Monitoring Apparatus" discloses a monitoring apparatus having a conductor, which is supported on a strip of woven fabric securable about a patient's torso. The fabric strip is stitched under tension by a plurality of longitudinally extending elastic stitches such that when the tension in the strip is released, the fabric becomes bunched or puckered along its entire length. An insulated wire conductor is stitched to one side of the fabric in a zigzag pattern. The stretching of the fabric in a longitudinal direction is accommodated by the puckers or folds with corresponding extension of the wire being accommodated by a widening and flattening of the saw tooth pattern. In use, the length of the band in its unstretched condition should be less than the circumference of the encircled portion of the torso of the patient such that the band may be stretched for a snug fit. To accommodate connection of the wire to the monitoring apparatus, the conductor is secured to the fabric such that both ends of the conductor terminate at the same longitudinal edge of the band. The ends of the conductor are soldered to connecting pins which are then secured in shrink tubing such that the tips of the connecting pins are exposed. The shrink tubing is stapled to the ends of the band. The conductors are then secured to a monitoring device.

The '640 Patent also discloses a RIP monitoring apparatus having a stretchable band. The stretchable band includes a piece of nonwoven fabric, and a piece of tissue paper secured to the nonwoven fabric. A piece of elastic material is adhesively secured between the nonwoven fabric and the tissue paper along a substantial portion of the length. The elastic material in a stretched condition when the first and second pieces of material are in a flat condition. As described above, the nonwoven fabric and the tissue paper define crosswise puckers when the elastic material is in an unstretched condition for accommodating stretching of the band when the elastic material is stretched. A conductor is adhesively secured between the nonwoven fabric and the tissue paper. A fastener, such as, for example, a hook and loop fastener, is secured to the opposing ends of the band for securing the band to the patient. Free ends of the conductor extend from the ends of the band are connected to a LC oscillator circuit contained a housing secured to one end of the band. The LC oscillator circuit is then electrically connected to a monitoring apparatus.

None of these RIP monitoring apparatus, however, are suited for mass production. Each of these devices has a rather complex construction, which results in higher manufacturing costs and final product costs. Due to the expense, it is impractical to discard them after a single use. Yet in the medical field, where sanitary considerations are paramount for sound medical reasons as well as psychological ones, it is preferred to render disposable any apparatus that comes into contact with the patient, such as occurs with the RIP bands. Furthermore, these RIP monitoring apparatus are cut in predetermined lengths and can not be easily sized to fit individual users. Hospitals would need to maintain a substantial inventory of different sized RIP bands.

OBJECTS OF THE INVENTION

It is accordingly an object of the present invention to provide a RIP band sensor device which overcomes the aforementioned drawbacks.

It is therefore an object of the present invention to provide a low cost sensor device for monitoring a patient's respiration that can be discarded after a single use.

It is another object of the present invention to provide a low cost RIP band sensor device that can be readily and easily sized to an individual.

It is another object of the present invention to provide a disposable sensor for monitoring the volume of an expandable organ during respiration.

It is a further object of the present invention to provide a RIP sensor device that can easily be connected to a monitoring apparatus.

It is yet a further object of the invention to provide a flexible RIP band that can be mass produced.

It is another object of the present invention to provide a connector assembly for a disposable sensor that establishes an electrical connections with a conductor wire in the disposable sensor.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative disposable sensor for monitoring and measuring the respiration of a patient. The disposable sensor includes at least one flexible band adapted to encircle a portion (e.g., the chest or abdomen) of the patient. A conductor strip is secured to the ribbon. It is contemplated that the conductor strips extends in a zig-zag or other predetermined pattern on the ribbon.

In accordance with the present invention, it is contemplated that the stretchable ribbon may include a first flexible ribbon of an elastomeric material, a second flexible ribbon of an elastomeric material secured to the first flexible ribbon of elastomeric material, and a conductor strip located between the first and second flexible ribbon of elastomeric material. The conductor strip extends in a zig-zag or other predetermined pattern between the first and second ribbon. In accordance with the present invention, it is contemplated that the first and second flexible ribbons are formed from a woven material. The first and second flexible ribbons are also formed from a thermoplastic elastomer.

The disposable sensor also includes a connector assembly for connecting and securing a first free end of the ribbon to a second free end of the ribbon. The connector assembly is operatively coupled to the conductor strip, and is further adapted to be connected to a monitoring device. In operation, changes in inductance of the conductor strip are transmitted through the connector assembly to the monitoring device.

In accordance with the present invention, the connector assembly for the disposable sensor includes a compression assembly for mechanically compressing the conductor strip. It is contemplated that the conductor strip may include a conductive wire having an outer insulation layer. The compression assembly cuts away the outer insulation layer.

It is also contemplated that the connector assembly of the disposable sensor may include a first connector portion for releasably receiving the first free end of the flexible ribbon. The first connector portion is adapted to engage a portion of the conductor strip located adjacent the first free end. The connector assembly also includes a second connector portion for releasably receiving the second free end of the flexible ribbon. The second connector portion being adapted to engage a portion of the conductor strip located adjacent the second free end.

The present invention is also directed to a method of measuring and monitoring changes in volume of an expandable organ of a patient. By measuring the changes in volume, the respiration of a patient may be measured and monitored. The method includes providing a supply of a flexible disposable sensor ribbon, cutting a length of the flexible disposable sensor ribbon to encircle a torso of the patient, securing a first end of the length to a releasable connector assembly, securing a second end of the length the releasable connector assembly, connecting the releasable connector assembly to a monitoring assembly, and monitoring changes in inductance of the flexible disposable sensor ribbon to measure and monitor the changes in volume of an expandable organ of the patient. The method further includes disposing of the length of the flexible disposable sensor ribbon after monitoring changes in inductance of the flexible disposable sensor band.

The present invention is also directed to an assembly apparatus for assembling a disposable RIP sensor band. The assembly apparatus includes a first supply assembly for supplying a first flexible ribbon, a second supply assembly for supplying a second flexible ribbon, and a conductor strip supply assembly for supplying the conductor strip. The supplies are positioned such that the conductor strip is located between the first flexible ribbon and second flexible ribbon. The assembly apparatus further includes a movable feeding assembly for feeding the conductor strip between the first and second flexible ribbons in a predetermined pattern, and a fixing assembly for fixing the first flexible ribbon to the second flexible ribbon such the conductor strip is secured therebetween in the predetermined pattern.

In accordance with the present invention, the fixing assembly may include a pair of pressing cylinders for applying pressure to the first and second flexible bands to sandwich the conductor strip therebetween. It is further contemplated that the fixing assembly may bond the first and second flexible ribbons together. The ribbons may be bonded together using heat or sound waves.

BRIEF DESCRIPTION OF THE DRAWINGS

The invention will be described in conjunction with the following drawings in which like reference numerals designate like elements and wherein.

DETAILED DESCRIPTION OF THE PREFERRED EMBODIMENTS

The flexible disposable RIP sensor ribbon in accordance with the present invention will now be described in detail. The RIP sensor ribbon 10 includes a single strip of flexible stretchable ribbon that can be easily cut to size for a particular patient from a supply of ribbon 10. The sensor ribbon 10 includes a conductor strip 13 secured thereto. The conductor strip 13 may be woven into the flexible ribbon. It is also contemplated that the conductor strip 13 may be suitably bonded to the ribbon. It is preferred that the conductor strip 13 be disposed in a zig-zag pattern, as show in FIG. 2, which permits flexing of the ribbon 10 as the patient breaths without damaging the conductor strips 13. While the zig zag pattern is preferred from a manufacturing and flexibility standpoint, other layouts of the conductor strip 13 are contemplated to be within the scope of the present invention provided the layout permits expansion and contraction of the ribbon 10.

Figure 2:
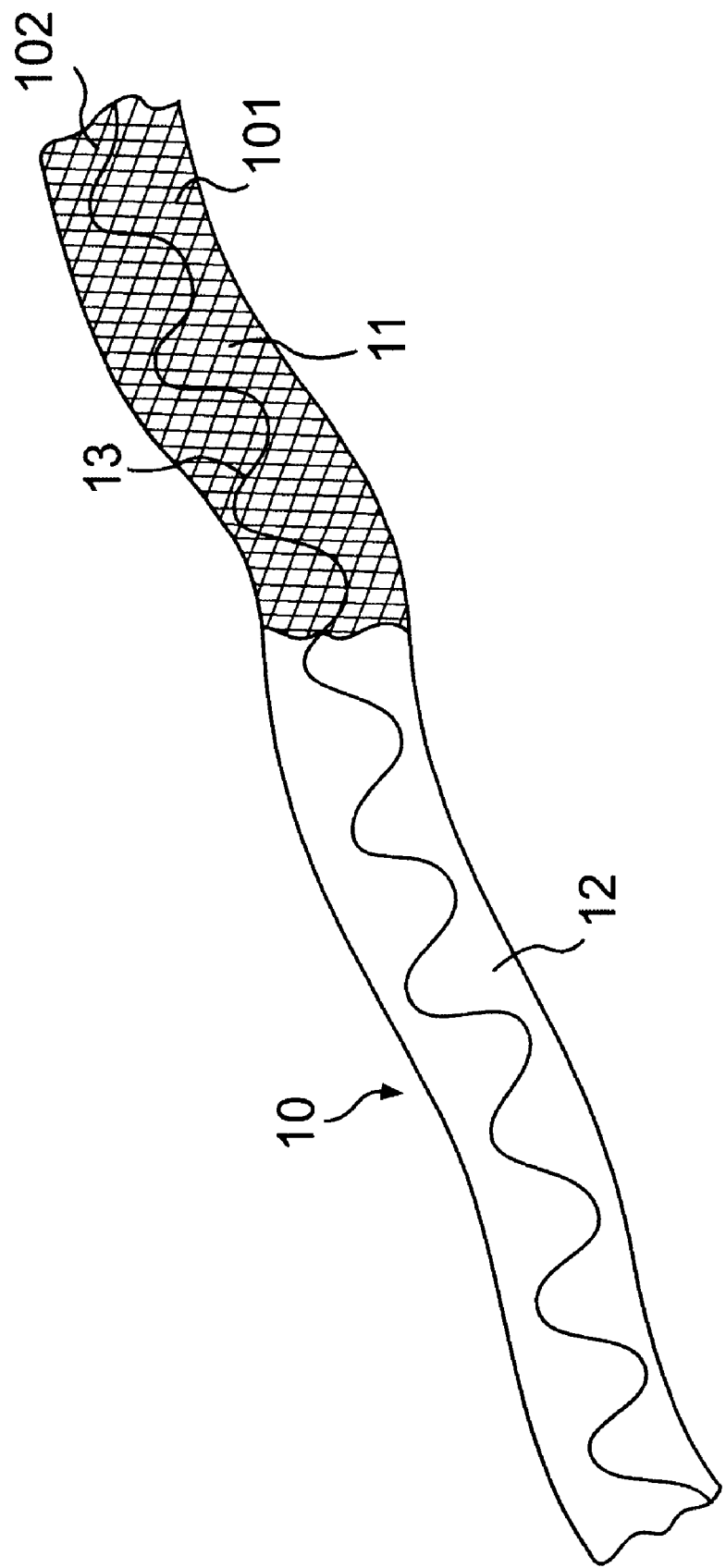
FIG. 2 is a partial schematic view of the RIP sensor band of FIG. 1.

The flexible ribbon 10 preferably has a woven construction, as partially shown in FIG. 2. The flexible ribbon 10 includes a plurality of longitudinally extending elongated strands 101. The strands 101 are flexible and elastic to permit expansion of the ribbon 10 in response to changes in volume of the expandable organ. A plurality of lateral strands 102 extend between the strands 10, as shown in FIG. 2. The lateral strands 102 are preferably formed of a flexible material that is not elastic. The strands 101 and 102 form a loosely woven flexible ribbon. It is contemplated that adjacent strands 101 may be spaced from each other. It is also contemplated that adjacent strands 102 may be spaced from each other.

It is also contemplated that the RIP sensor ribbon 10 may have a laminated construction. In accordance with one embodiment, the ribbon 10 includes a first flexible ribbon 11 and a second flexible ribbon 12. The flexible ribbons 11 and 12 are formed from an elastomeric material that is capable of expansion and retraction in response to respiration of a patient. The flexible ribbons are preferably from a thermoplastic plastic elastomer. It, however, is contemplated that the flexible ribbons 11 and 12 in accordance with the present invention may be formed from any elastomer or similar material that is suitable for heat welding and/ or high frequency welding. The width of the ribbons is preferably between 25 and 30 mm. It, however, is contemplated that other widths may be employed to monitor and measure volume changes in an expandable organ and thus the respiration of the patient. The RIP sensor ribbon 10 further includes a conductor strip 13 sandwiched between the flexible ribbons 11 and 12. As described above, the conductor strip 13 is disposed in a zig-zag pattern, as show in FIG. 2, which permits flexing of the ribbon 10 as the patient breaths without damaging the conductor strips 13.

Figure 8:
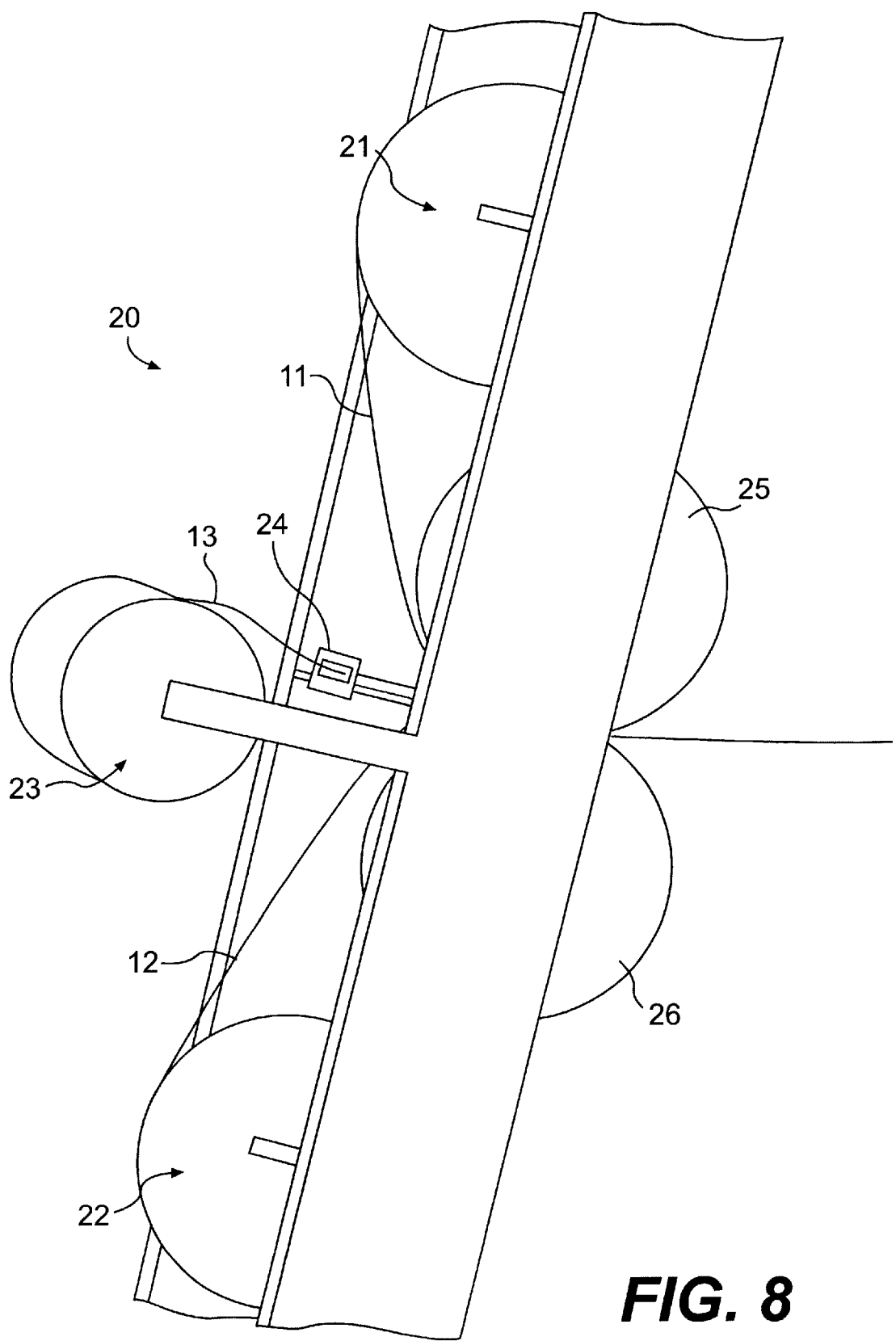
FIG. 8 is a schematic view of the assembly apparatus for manufacturing the RIP sensor band in accordance with the present invention.

The manufacture of the laminated ribbon 10 will now be described. It will be readily apparent to one of ordinary skill in the art that the sensor ribbon 10 in accordance with the present invention can be easily mass produced at low cost. As such, it is not impractical to discard the ribbon 10 after a single use. In accordance with the present invention, an assembly apparatus 20, shown in FIG. 8, is provided for the manufacture of the ribbon 10. The assembly apparatus 20 includes a first ribbon supply 21 for supplying a feed of the first flexible ribbon 11 and a second ribbon supply 22 for supplying a feed of the second flexible ribbon 12. The assembly apparatus 20 also includes a conductor strip supply 23. The conductor strip supply 23 is adapted to feed the conductor strip 13 such that is placed between the first and second ribbons 11 and 12. Prior to placement between the first and second ribbons 11 and 12, the conductor strip 13 is fed through a movable feeding assembly 24. The movable feeding assembly 24 moves from left to right, which creates the zig-zag pattern of the conductor strip 13 between the ribbons 11 and 12. The patterned conductor strip 13 and the ribbons 11 and 12 are then pressed together between pressing cylinders 25 and 26.

It is contemplated that the pressing force supplied by the pressing cylinders 25 and 26 is sufficient to pull the ribbons 11 and 12 from the first and second supplies 21 and 22. It is further contemplated that the pressing force supplied by the pressing cylinders 25 and 26 is sufficient to pull the conductor strip 13 from the conductor strip supply 23. The present invention, however, is not limited to these supply assemblies. The use of a mechanical feed for one or more the supplies 21, 22 and 23 is considered to be well within the scope of the present invention.

The welding or bonding operation for securing the first ribbon 11 to the second ribbon 12 may be performed by the pressing cylinders 25 and 26. It is also contemplated that the welding operation may be performed by a separate welding and/or bonding station downstream from the pressing cylinders 25 and 26. The laminated RIP sensor ribbon 10 may then be suitably packaged. For example, the sensor ribbon 10 may be wound around a roll, not shown, for easy dispensing in a hospital. Alternatively, the ribbon 10 may be placed in an appropriate dispensing box.

Figure 1:
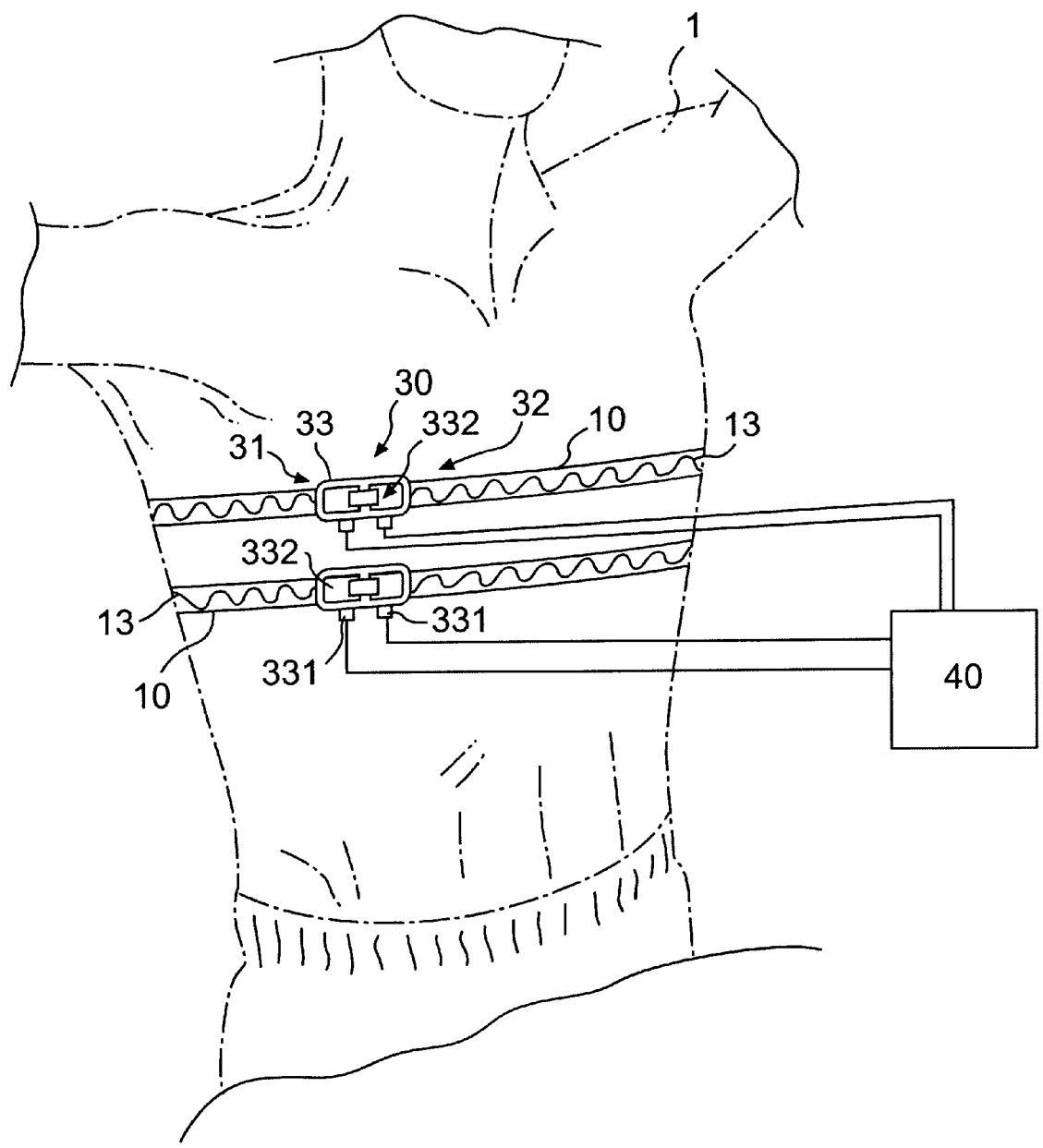
FIG. 1 is a view of the RIP sensor ribbon in accordance with the present invention located on a patient.
Figure 3:
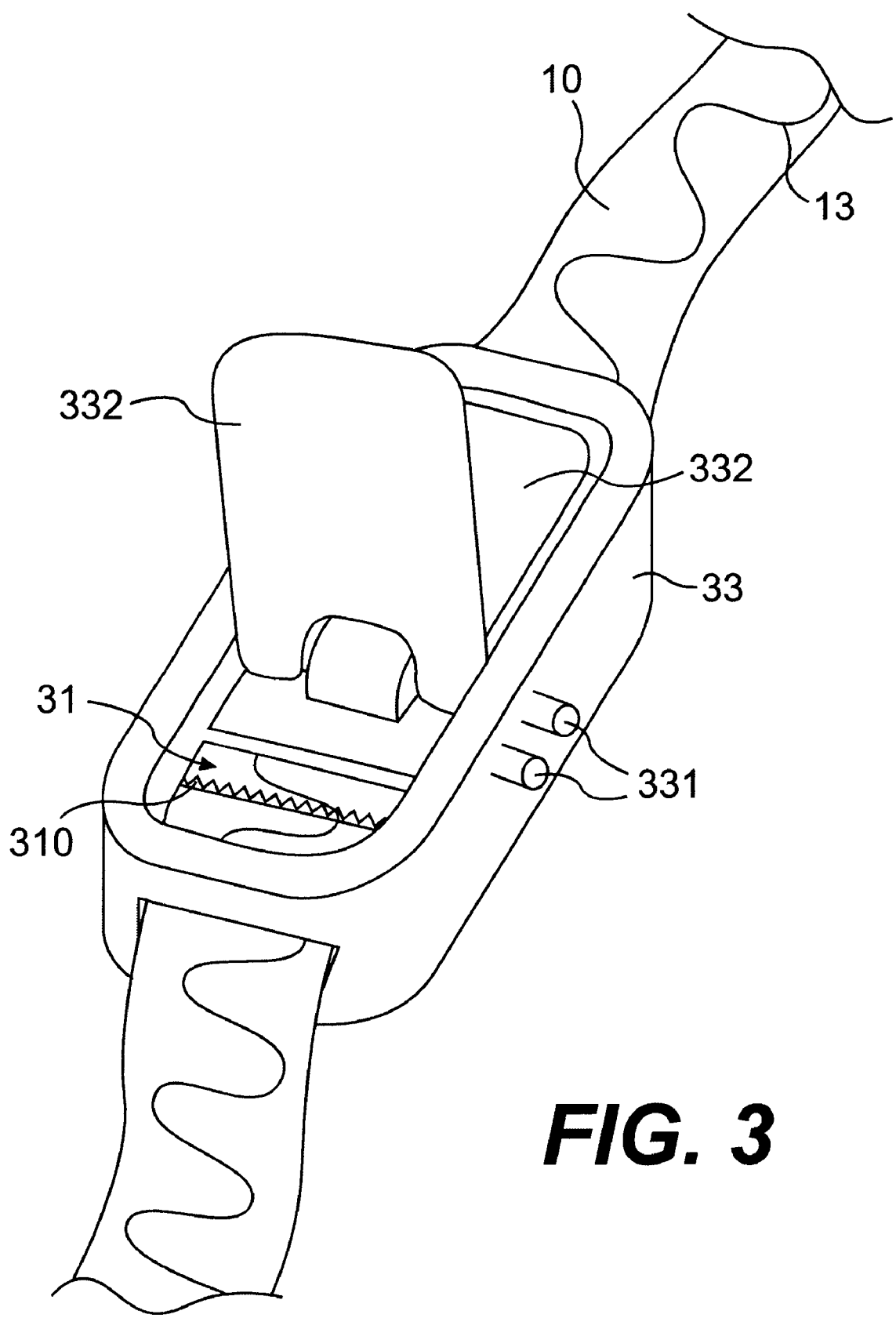
FIG. 3 is a schematic view illustrating the connector assembly and RIP sensor ribbon in accordance with the present invention.

The operation and use of the RIP sensor ribbon 10 connected to a connector assembly 30 to measure and monitor the respiration of a patient will now be described. The technician or health care provider dispenses a sufficient length of ribbon 10 from the dispensing box or roll to encircle the abdomen of the patient 1, as shown in FIG. 1. The length of ribbon 10 is then cut. A first end of the ribbon 10 is secured to a first connector portion 31 of a connector assembly 30, as shown in FIG. 3. The first connector portion 31 includes a piercing assembly 310 for piercing and engaging the ribbon 10. The piercing assembly 310 also makes contact with the connector 13 within the ribbon 10. A second end of the ribbon 10 is secured to a second connector portion 32 of the connector assembly 30. Like the first connector assembly 31, the second connector portion 32 includes a piercing assembly for piercing and engaging the ribbon 10. The piercing assembly also makes contact with the connector 13 within the ribbon 10.

The ribbon 10 is then stretched around the torso of the patient. The first and second connector assemblies 31 and 32 are then secured to the housing 33 of the connector assembly 30. The housing 33 includes connection outputs 331. A monitoring apparatus 40 is electrically connected to the connection outputs 331, as shown in FIG. 1. The housing 33 further includes a latching mechanism 332 for securing the connector assemblies 31 and 32 within the housing 33. After the ribbon 10 is secured to the patient and the monitoring apparatus 40 is connected to the connection outputs 331, changes in inductance in the conductor strip 13 corresponding to the respiration of the patient can measured and monitored. These changes in inductance are converted to an electrical signal for the conductive loop, the signal is calibrated by the electronic monitoring device to accurately measure the volume of respiration. The monitoring device 40 can then monitor and record the respiration of the patient.

It is contemplated that more than one ribbon 10 may be used to encircle the chest and abdomen of the patient, as shown in FIG. 1. A separate connector assembly 30 is used for each ribbon 10. The separate ribbons 10 may be connected to a single monitoring device 40.

After the monitoring operation is complete, the ribbon 10 can be removed from the patient. The ribbon 10 can be disconnected from the connector assembly 30 and discarded.

It is contemplated that the connector assembly 30 may be disposed of after use or reused if desired. The present invention permits the sizing of the sensor 10 to be patient specific. Unlike the prior art, it is not necessary for a hospital to maintain a large supply of different sized sensors for different patients.

The operation and use of the RIP sensor ribbon 10 connected to a preferred connector assembly 50 to measure and monitor the respiration of a patient will now be described. Like the embodiment described above, the technician or health care provider dispenses a sufficient length of ribbon 10 from the dispensing box or roll to encircle the abdomen of the patient 1, as shown in FIG. 1. The length of ribbon 10 is then cut. A first end of the ribbon 10 is secured to a female connector portion 51 of a connector assembly 50, as shown in FIG. 3. A second end of the ribbon 10 is secured to a male connector portion 52 of the connector assembly 50.

Figure 4:
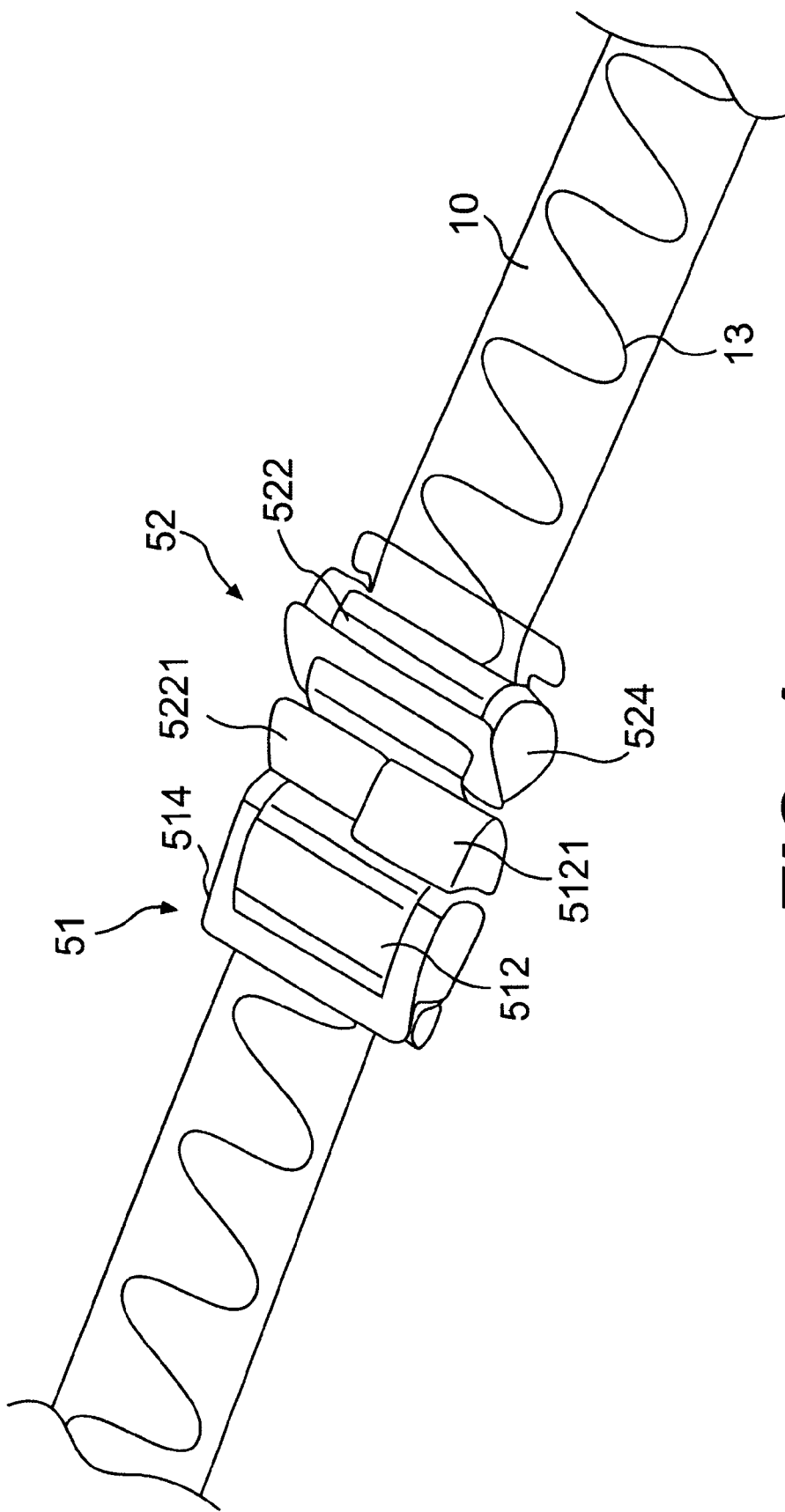
FIG. 4 is a schematic view illustrating a preferred connector assembly and RIP sensor ribbon in accordance with the present invention.
Figure 5:
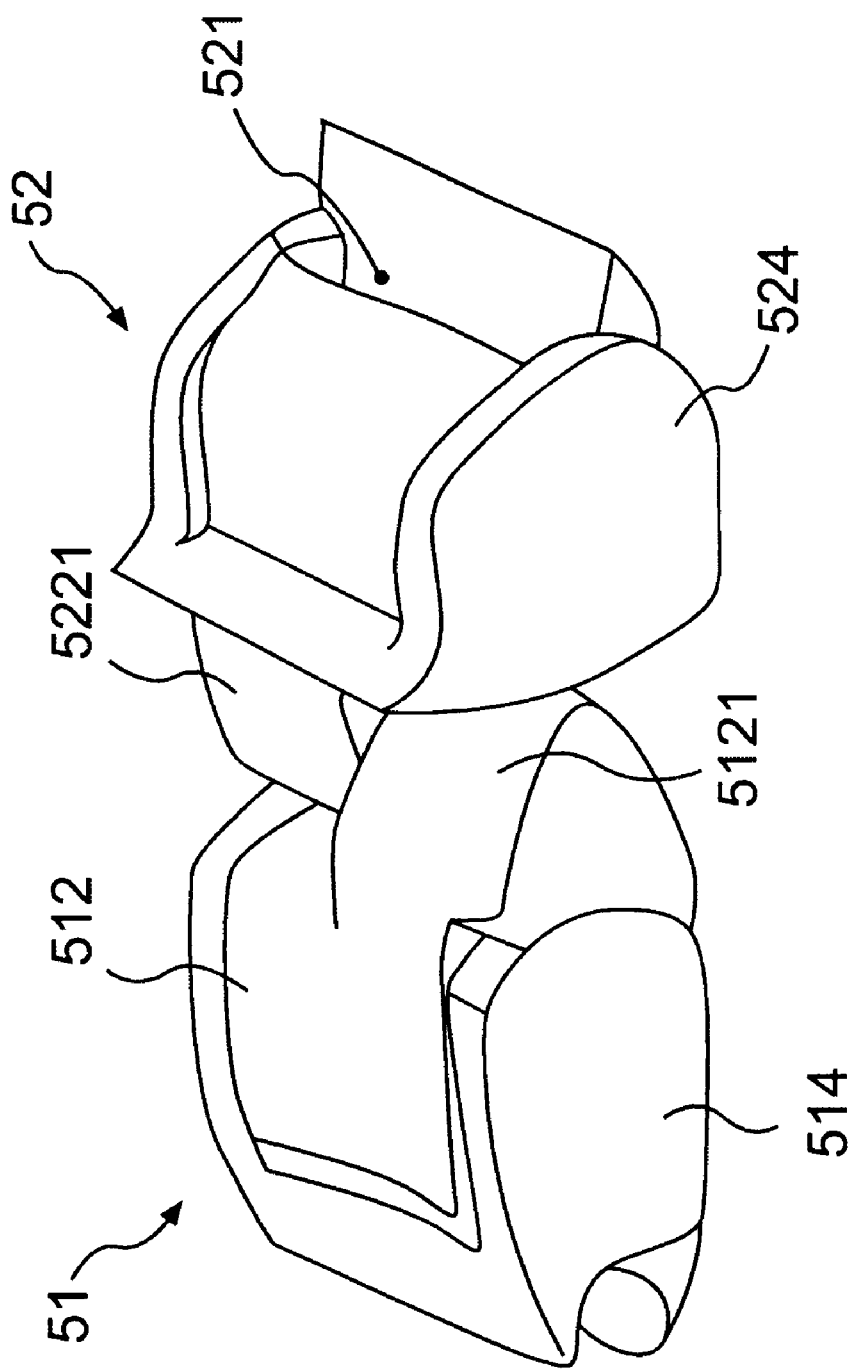
FIG. 5 is an enlarged schematic view of the connector assembly of FIG. 4.
Figure 6:
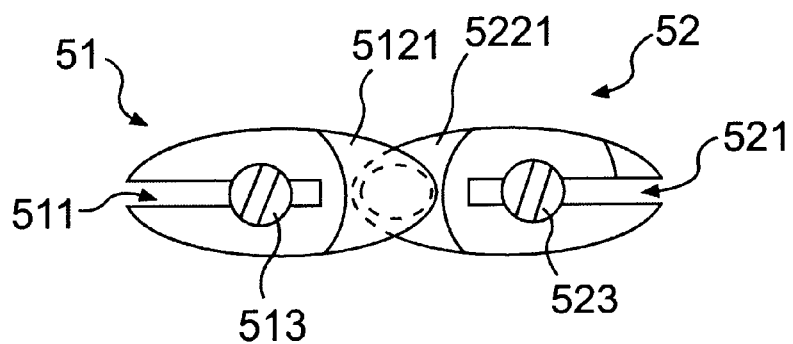
FIG. 6 is a partial schematic view of the male and female connector assemblies of the connector assembly of FIG. 4 in a closed engaged position.

The ribbon 10 is then stretched around the torso of the patient. The female and male connector assemblies 51 and 52 are then engaged, as shown in FIGS. 4 and 6. The connector assembly 50 is then secured to the monitoring apparatus 40. After the ribbon 10 is secured to the patient and the monitoring apparatus 40, changes in inductance in the conductor strip 13 corresponding to volume changes in an expandable organ during respiration of the patient can measured and monitored. These changes in inductance are converted to an electrical signal for the conductive loop, the signal is calibrated by the electronic monitoring device to accurately measure the volume of respiration. The monitoring device 40 can then monitor and record the respiration of the patient.

Figure 7:
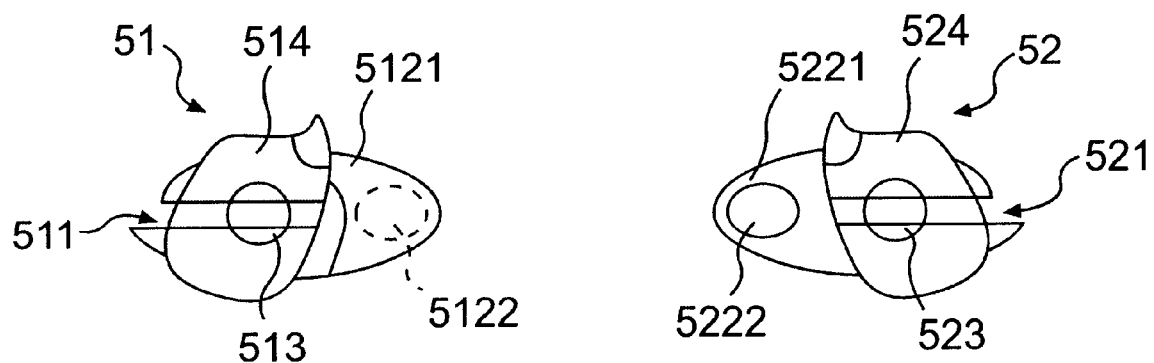
FIG. 7 is a partial schematic view of the male and female connector assemblies of the connector assembly of FIG. 4 in an open disengaged position.

The first end of the ribbon 10 is secured to the female connector portion 51 by inserting the ribbon 10 into the channel 511, shown in FIG. 7. The channel 511 extends through a stationary housing portion 512 and a rotatable member 513. The rotatable member 513 is secured to a rotatable actuator assembly 514. The rotatable actuator assembly 514 rotates between an open position, shown in FIG. 7, and a closed position, shown in FIG. 6.

When in the closed position, shown in FIG. 6, the ribbon 10 and, in particular, the conductor strip 13 is compressed between the rotatable actuator assembly 514 and the stationary housing portion 512. With this arrangement, any protective coating on the conductor strip 13 is stripped as the actuator assembly 514 rotates to the closed position. The compression of the conductor strip 13 establishes an electrical connection between the strip 13 and the female connector assembly 51. The female connector assembly 51 can then be connected to the monitoring apparatus 40 in a similar manner as described above in connection with connector assembly 30.

The second end of the ribbon 10 is secured to the male connector portion 52 by inserting the ribbon 10 into the channel 521, shown in FIG. 7. The channel 521 extends through a stationary housing portion 522 and a rotatable member 523. The rotatable member 523 is secured to a rotatable actuator assembly 524. The rotatable actuator assembly 524 rotates between an open position, shown in FIG. 7, and a closed position, shown in FIG. 6.

Like the female connector assembly 51, the conductor strip 13 is compressed between the rotatable actuator assembly 524 and the stationary housing portion 522. With this arrangement, any protective coating on the conductor strip 13 is stripped as the actuator assembly 524 rotates to the closed position. The compression of the conductor strip 13 establishes an electrical connection between the strip 13 and the male connector assembly 52. The male connector assembly 52 can then be connected to the monitoring apparatus 40 in a similar manner as described above in connection with connector assembly 30.

The female connector assembly 51 and male connector assembly 52 can be releasably secured together in the following manner. The stationary housing portion 512 includes an engagement portion 5121 having an engagement recess 5122 formed therein, as shown in FIG. 7. The recess 5122 is adapted to releasably receive an engagement projection 5222 on engagement portion 5221 of the male connector assembly 52. It is contemplated that other suitable means may be used to secure the connector assemblies 51 and 52 together.

It is contemplated that more than one ribbon 10 may be used to encircle the chest and abdomen of the patient, as shown in FIG. 1. A separate connector assembly 30 or 50 may used for each ribbon 10. The separate ribbons 10 may be connected to a single monitoring device 40.

After the monitoring operation is complete, the ribbon 10 can be removed from the patient. The ribbon 10 can be easily disconnected from either connector assembly 30 or 50 and discarded. It is contemplated that the connector assembly 30 or 50 may be disposed of after use or reused if desired. The present invention permits the sizing of the sensor 10 to be patient specific. Unlike the prior art, it is not necessary for a hospital to maintain a large supply of different sized sensors for different patients.

It will be apparent to those skilled in the art that various modifications and variations may be made without departing from the scope of the present invention. Thus, it is intended that the present invention covers the modifications and variations of the invention, provided they come within the scope of the appended claims and their equivalents.

What is claimed is:

1. A disposable sensor for monitoring changes in volume of an expandable organ of a patient, comprising:

at least one flexible stretchable ribbon adapted to encircle a portion of the patient, wherein each of said at least one flexible stretchable ribbon includes a conductor secured thereto, wherein each of said at least one flexible stretchable ribbon has a first free end and a second free end, wherein the conductor has a first conductor free end adjacent the first free end and a second conductor free end adjacent the second free end; and a connector assembly for connecting and securing said first free end to said second free end, wherein said connector assembly is operatively coupled to said conductor adjacent the first conductor free end and the second conductor free end, and is adapted to be connected to a monitoring device such that said connector assembly transmits changes in inductance of said conductor to the monitoring device.

2. The disposable sensor according to claim 1, wherein said conductor is secured to said flexible stretchable ribbon in a zig zag pattern.

3. A disposable sensor for monitoring changes in volume of an expandable organ of a patient, comprising:

at least one flexible stretchable ribbon adapted to encircle a portion of the patient, wherein each of said at least one flexible stretchable ribbon includes a conductor secured thereto, wherein each of said at least one flexible stretchable ribbon has a first free end and a second free end; and a connector assembly for connecting and securing said first free end to said second free end, wherein said connector assembly is operatively coupled to said conductor, and is adapted to be connected to a monitoring device such that said connector assembly transmits changes in inductance of said conductor to the monitoring device, wherein said connector assembly includes a compression assembly for mechanically compressing said conductor.

4. The disposable sensor according to claim 3, wherein said conductor comprises a conductive wire having an outer insulation layer, wherein said compression assembly cuts away said outer insulation layer.

5. The disposable sensor according to claim 1, wherein each of said at least one flexible stretchable ribbon comprises:
   a first flexible ribbon; and
   a second flexible ribbon secured to said first flexible ribbon, wherein said conductor is located between said first and second flexible ribbons.

6. The disposable sensor according to claim 5, wherein said conductor is laminated between said first flexible ribbon and said second flexible ribbon.

7. The disposable sensor according to claim 5, wherein said conductor is disposed between said first flexible ribbon and said second flexible ribbon in a zig zag pattern.

8. The disposable sensor according to claim 5, wherein each of said first and second flexible ribbons is formed from a thermoplastic elastomer.

9. The disposable sensor according to claim 1, wherein said connector assembly comprising:
   a first connector portion for releasably receiving said first free end of said flexible ribbon, wherein said first connector portion being adapted to engage a portion of said conductor located adjacent said first conductor free end; and
   a second connector portion for releasably receiving said second free end of said flexible ribbon, wherein said second connector portion being adapted to engage a portion of said conductor located adjacent said second conductor free end.

10. A disposable sensor for monitoring changes in volume of an expandable organ of a patient, comprising:
    at least one flexible stretchable ribbon adapted to encircle a portion of the patient, wherein each of said at least one flexible stretchable ribbon includes a conductor secured thereto, wherein each of said at least one flexible stretchable ribbon has a first free end and a second free end; and
    a connector assembly for connecting and securing said first free end to said second free end, wherein said connector assembly is operatively coupled to said conductor, and is adapted to be connected to a monitoring device such that said connector assembly transmits changes in inductance of said conductor to the monitoring device, wherein said connector assembly comprising:
       a first connector portion for releasably receiving said first free end of said flexible ribbon, wherein said first connector portion being adapted to engage a portion of said conductor located adjacent said first free end; and
       a second connector portion for releasably receiving said second free end of said flexible ribbon, wherein said second connector portion being adapted to engage a portion of said conductor located adjacent said second free end, wherein each of said first connector portion and said second connector portion includes a compression assembly for mechanically compressing said conductor.

11. The disposable sensor according to claim 10, wherein said conductor includes a conductive wire having an outer insulation layer, wherein said compression assembly cuts away said outer insulation layer.

12. The disposable sensor according to claim 1, wherein each of said at least one flexible stretchable ribbon has a woven construction.

13. The disposable sensor according to claim 12, said stretchable ribbon comprises:
    a plurality of longitudinally extending flexible strands; and
    a plurality of laterally extending flexible strands, wherein said each of said laterally extending flexible strands interconnects said plurality of longitudinally extending flexible strands.

14. The disposable sensor according to claim 13, wherein said plurality of longitudinally extending flexible strands are formed from an elastic material.

15. The disposable sensor according to claim 14, wherein each of said flexible stretchable ribbon comprises:
    a first flexible ribbon having a woven construction; and
    a second flexible ribbon having a woven construction secured to said first flexible ribbon, wherein said conductor is located between said first and second flexible ribbons.

16. A method of measuring and monitoring changes in volume of an expandable organ of a patient, comprising:
    providing a supply of a flexible disposable sensor ribbon;
    cutting a length of the flexible disposable sensor ribbon to encircle a torso of the patient;
    securing a first end of the length to a releasable connector assembly;
    securing a second end of the length the releasable connector assembly;
    connecting the releasable connector assembly to a monitoring assembly; and
    monitoring changes in inductance of the flexible disposable sensor ribbon to measure and monitor the volume changes in the expandable organ of the patient.

17. The method according to claim 16, wherein the flexible disposable sensor ribbon comprises a flexible stretchable ribbon having a conductor secured thereto.

18. The method according to claim 16, wherein said securing a first end of the length of ribbon to a releasable connector assembly includes connecting the conductor to the releasable connector assembly, and said securing a second end of the length of ribbon to the releasable connector assembly includes connecting the conductor to the releasable connector assembly.

19. The method according to claim 18, wherein the releasable connector assembly includes a first connector portion for releasably receiving the first end of the length of ribbon, and a second connector portion for releasably receiving the second free end of the length of ribbon.

20. The method according to claim 16, further comprising:
    disposing of the length of the flexible disposable sensor ribbon after monitoring changes in inductance of the flexible disposable sensor ribbon.

* * * * *